United States Patent
Tiefnig

[11] Patent Number: 5,854,557
[45] Date of Patent: Dec. 29, 1998

[54] CORROSION MEASUREMENT SYSTEM

[76] Inventor: Eugen Tiefnig, 3653 Lost Nation Rd., Willoughby, Ohio 44094

[21] Appl. No.: 763,974

[22] Filed: Dec. 10, 1996

Related U.S. Application Data

[63] Continuation-in-part of Ser. No. 229,449, Apr. 18, 1994, Pat. No. 5,583,426.

[30] Foreign Application Priority Data

Apr. 16, 1993 [AU] Australia ............................. A760/93-1

[51] Int. Cl.⁶ ........................... G01N 17/04; G01N 27/26
[52] U.S. Cl. ........................ 324/700; 324/71.2; 204/404; 205/775.5; 205/777
[58] Field of Search ................. 324/700, 71.1, 324/71.2; 204/404; 205/775.5, 777; 422/53

[56] References Cited

U.S. PATENT DOCUMENTS

| | | | |
|---|---|---|---|
| 3,069,332 | 12/1962 | Seyl | 205/775.5 |
| 3,406,101 | 10/1968 | Kilpatrick | 205/777 |
| 3,660,249 | 5/1972 | Townsend | 205/775.5 |
| 3,766,042 | 10/1973 | Wilson | 324/71.2 |
| 4,019,133 | 4/1977 | Manley et al. | 324/700 |
| 4,061,965 | 12/1977 | Nelson | 205/730 |
| 4,328,462 | 5/1982 | Jensen | 324/229 |
| 4,468,613 | 8/1984 | Slough et al. | 324/71.2 |
| 4,587,479 | 5/1986 | Rhoades et al. | 324/71.2 |
| 4,806,850 | 2/1989 | Saumade et al. | 324/71.1 |
| 4,843,319 | 6/1989 | Lara | 324/240 |
| 4,881,037 | 11/1989 | Bellingham et al. | 324/425 |
| 5,087,873 | 2/1992 | Murphy et al. | 324/71.2 |
| 5,126,654 | 6/1992 | Murphy et al. | 324/71.2 |
| 5,132,620 | 7/1992 | Rempt | 324/244.1 |
| 5,188,715 | 2/1993 | Chen et al. | 204/153.11 |
| 5,243,297 | 9/1993 | Perkins et al. | 324/700 |

*Primary Examiner*—Glenn W. Brown
*Attorney, Agent, or Firm*—Joseph H. Taddeo

[57] ABSTRACT

An improved corrosion measurement system for determining the rate of corrosion of a fluid medium. The system is comprised of a highly sensitive excitation and amplification electronic circuitry for registering and displaying the stable and accurate measurement results. A unique unitized measurement probe is temperature stabilized using thermally inertially balanced metallic probes; the first reference element being coated with an impermeable insulating coating, the second, the corroding element, being fully exposed to the corrosive fluid medium.

28 Claims, 8 Drawing Sheets

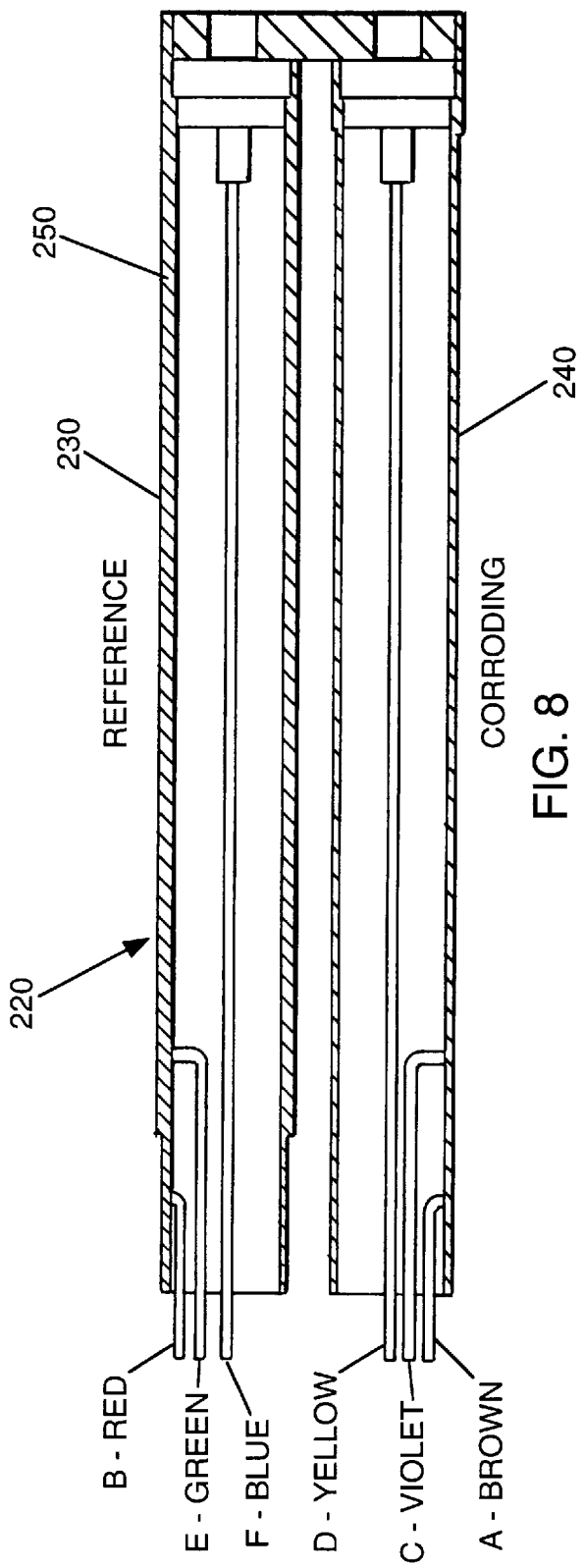
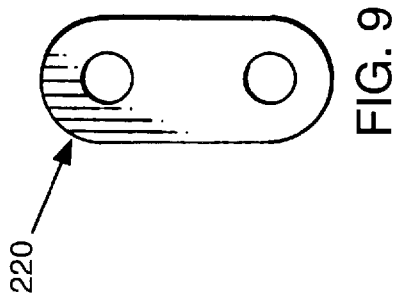
FIG. 8
FIG. 9

CORROSION MEASUREMENT SYSTEM

REFERENCE TO PREVIOUSLY FILED APPLICATIONS

This is a Continuation-in-Part of application Ser. No. 08/229,449, filed Apr. 18, 1994; issued Dec. 10, 1996, U.S. Pat. No. 5,583,426. Your applicant respectfully claims the benefit of that earlier patent filing date, Apr. 18, 1994, in the United States under 35 U.S.C. §120, and 37 CFR §1.53a.

In that prior application Ser. No. 08/229,449, filed Apr. 18, 1994, your Applicant sought foreign priority for Austrian Patent No. A760/93-1, filed Apr. 16, 1993. The applicant also claims foreign priority pursuant to 35 U.S.C. 119 and 37 CFR §1.55(a), for the Austrian (national) patent, identified as follows:

- date of filing the Austrian (national) patent: Apr. 16, 1993;
- Austrian Patent Office reference number: A760/93-1;
- International Patent Classification: GO1N;
- Inventor: Eugen Tiehig;
- Original Title: Verfahran und Vorrichtung zur Ermittlung der Korrosivitat Method and Device for Determining Corrosivity)

FIELD OF THE INVENTION

This invention concerns a new procedure and equipment to measure corrosion of metallic materials exposed to fluid media. More particularly, the invention relates to measurement of corrosion, especially electrochemical corrosion and erosion of iron alloys in moving fluids. The present invention further relates to an improved corrosion measurement system, and more particularly to a highly sensitive corrosion measurement system to determine the rate of corrosion simply, effectively and accurately without sacrificing repeatability; the corrosion measurement system comprising a novel unitized probe and a unique measuring and display unit.

BACKGROUND OF THE PRESENT INVENTION

Electrochemical corrosion pertains to destruction of the surface of a metal by electrochemical reaction. Such corrosion occurs if an electrolytic solution contacts the junction of two different metals. The corrosion element may be termed a short-circuited galvanic element.

On the elements anode, the less noble metal is oxidized. At the cathode, oxygen or hydrogen ions are reduced. Oxygen corrosion occurs in a neutral or alkali solution; while hydrogen corrosion is the result in solutions of higher pH or acidic solutions.

Electrochemical corrosion is a threat wherever two metallic conductors are in contact. Even foreign elements on a metallic surfaces may cause electrochemical corrosion. A film of water can be sufficient for electrolyte formation by exposure of metallic surfaces to the atmosphere. The rate of electrochemical corrosion is dependent upon conductivity of the electrolyte. Carbon dioxide absorption from ambient air can be partially transformed to carbonic acid in water, thereby contributing to electrochemical corrosion. Industrial emissions with sulfur dioxide, nitrogen oxides, acid gases, ammonia, amine and oxidizing gases and vapors increase the likelihood for metallic corrosion.

Protection from corrosion generally involves these considerations:

a) Positioning identical or electrochemically similar metals and alloys in a given milieu;

b) Preventing contact of electrolytic solutions with the junction between two different metals by application of protective coverings, coatings or metallic coverings; and c) Cathodic protection can prevent corrosion of metals exposed to an electrolytic environment by electrically connecting the corrodible metal to a sacrificial anode made of a metal higher in the electromotive series than the metal for protection, i.e., a metal that is anodic to the material for protection. When the protected metal and the electrically connected sacrificial anode are both disposed within the same electrolytic environment, a galvanic cell is formed in which the protected material is the cathode, whereby metal atoms on the exposed surface of the sacrificial anode are ionized by the surrounding electrolyte and go into solution and the protected metal does not corrode since free electrons are readily available at the surface of that structure to chemically reduce or neutralize positive ions that reach the surface of the protected material.

Various measuring methods have been utilized in the field of protection against corrosion. Impedance spectroscopy, measurement of oxygen, hydrogen and pH value in solution, the redox potential, and weight control of metallic specimens inserted into the medium and determination of resistance.

Electrical resistance measurement is achieved with by insertion of pieces of wire, tubes or disks into the medium and exterior measurements indicating corrosion from the medium are taken. The change, diminution of size of the object, increases the resistance of the metallic specimen and, therefore, directly relates to the loss of metal by corrosion and/or erosion. The data can be converted to unit loss of metal per time unit to provide corrosion rate per year or similar time period.

Disadvantages concomitant with electrical resistance technique include the fact that the specimen itself is subjected to the signal current, for there is no galvanic separation between the metallic specimen and the medium to be measured. Furthermore, wire specimens are unstable and when used in a fluid moving at high rate, special protective devices for the metal specimen are required. Temperature compensation is unreliable due to disparity of the sacrificial and reference specimens. Changes in resistance of the specimens due to diminution of mass are small and range within milli and micro-Ohms. As such, recordation of signals is difficult and readily subject to extraneous influences. Also, the measurements can be erroneous in stronger electrolytes or by existence of electrical conducting depositions on the specimen.

Other modem sensors for corrosion measuring devices are "linear Polarization Probes", "Hydrogen Probes" and probes for impedance spectroscopy.

Recent reports from Russia indicate development of a method for magnetic measurements for the loss of mass due to corrosion of reinforcements in concrete bridge constructions by the use of "SQUID" gradiometers. Only initial tentative experiments have been reported.

The foregoing disclosures, however, have been found unsatisfactory in many respects. The disadvantage of these procedures is that they cannot be used on a technically large scale; they may be unreliable for sensitivity to extraneous influences; they may not be sufficiently durable and require repetitive calibration.

SUMMARY OF THE INVENTION

In view of the various limitations and deficiencies in the foregoing prior art, general objects of the present invention are to provide a method and apparatus to determine the loss of mass of metallic material due to corrosion and erosion; under technically difficult conditions and in aggressive media; unimpeded by foreign influences; and, to obtain signal measurements with sufficient signal sizes to expedite the measuring process with highly reproducible results.

These and other goals are achieved by contacting the medium with a specimen within a probe or sensor formed as a core or yoke having a magnetic field from at least one coil with a set current and the probe or sensor set in a constant position in the medium. Corrosion and erosion of the specimen with resultant diminution in mass gives resultant change of at least one magnetic value, preferably inductance, relative to inductive resistance in the coil of the sensor, whereby the electromagnetic measurement unit can be derived.

Of the above-mentioned probes, the E/R (Electrical Resistance) probes are similar to the M/R (Magnetic Resistance) probes described herein. Function of the probes can be contrasted as follows:

E/R probes: Loss of metal by corrosion or erosion gives increased resistance in Ohms for the sensor-element which is charged with DC current.

M/R probes: Loss of metal by corrosion or erosion of the sensor element results in diminution of inductance of the sensor coil/specimen system.

Non-electric characteristics of a fluid can influence the resistance of the sensor and, further, such non-electric quantities can also alter the inductance of the specimen.

The procedure for determining the corrosivity and/or erosivity of fluid media respective to the change of mass of metallic materials such as iron, more specifically steel, which come into or are in contact with fluid media causing corrosion and/or erosion especially in a moving or streaming media, whereby testing is achieved by equipment having a composition and/or structure identical or corresponding to the metallic material exposed and held in contact in the fluid media during a given time span and the change, particularly loss of mass, registered and determined as an electrical measurement and devices facilitating the carrying out of this procedure, comprising a sensor or probe having at least one probe, with a core and/or a yoke within the magnetic field of at least one coil, connected or connectable to an alternating current, under constant geometric circumstances, is brought into contact with a fluid media and the change in mass of the probe, especially the reduction due to corrosion and/or erosion is reflected in the change of at least one magnetic quantity, preferably the inductance respective to the inductive resistance of the system consisting of coils and probe, specifically the sensor's coil response on the sensor's coils, or in an electrical quantity derived from those electromagnetic quantities whereby the corrosivity of a fluid is determined.

The present invention is further directed to an improved corrosion measurement system that is comprised of a novel measurement probe and newly designed measurement circuitry. This highly sensitive corrosion measurement system determines the rate of corrosion simply, effectively and accurately with repeatable results.

The measurement probe is comprised of two basic elements, a reference element and a corroding element. The reference element is conformally coated with a protective impermeable material to prevent the corrosive medium from etching or decomposing it, when the probe is immersed into the corrosive medium; whereas, the corrosion measurement element of the probe is not coated with the protective material and remains fully exposed to the corrosive medium.

It is essential that the protective coating material has excellent thermal transfer characteristics to obtain good thermal tracking readings between the reference and corroding elements. Further, this coating must also have good electrical insulating properties.

Both electrodes, including the reference and the corroding element, are made of the same metals and of the same physical geometry, such as the mass, the diameters, thickness, and the lengths. Because each electrode has near identical physical properties, the errors caused by thermal gradients are eliminated. The ratio of the voltages across each element is thermally compensating, thereby eliminating errors due to thermal tracking.

To further compensate for variations in temperature of the measuring circuitry, thermal compensation is accomplished by switching from the reference channel to the corroding channel before each measurement is made. The initial offset that was measured is subsequently subtracted from each of the corroding measurements taken for the removal of the temperature differential.

It is therefore an object of the present invention to provide an improved corrosion measurement system that is comprised of a novel measurement probe and newly designed measurement circuitry.

It is another object of the present invention to provide an improved corrosion measurement system that utilizes a unitized probe that houses matched electrodes to measure the rate of corrosivity of a fluid medium.

It is still another object of the present invention to provide an improved corrosion measurement system that utilizes a unitized probe that houses physically matched electrodes to thermally compensate each measurement, by having the temperature gradient between the reference element and the corroding element, be near zero because of the thermal tracking due to the equality of the thermal inertia of the two masses.

Yet, it is another object of the present invention to provide an improved corrosion measurement system that offers thermal compensation of the measurement circuitry by reading each channel, taking the difference between the two readings and then subtracting this difference reading from all subsequent reading of the corroding channel.

Still, it is another object of the present invention to provide an improved unitized probe that has a reference electrode coated with an impermeable material, that protects the reference electrode from the chemical and physical corrosion of the corrosive medium.

One additional object of the present invention to provide an improved unitized probe that has a reference electrode coated with an impermeable insulating material, that protects the user from any possible shock hazard.

It is a final object of the present invention to provide an improved newly designed measurement circuitry that is temperature stable and is highly sensitive to measure the voltage differences that are derived from the reference and corroding channel to present that rate of corrosion of the corrosive medium.

These and other advantages of the present invention will become more apparent upon further reading of the detailed specification. It should be understood that deviations or modifications can be made without deviating or departing from the spirit of the present invention.

DESCRIPTION OF THE DRAWINGS

FIG. 8 depicts a side elevation of the unitized measurement probe of an alternate embodiment, where only the probe ends are immersed in the corrosive fluid.

FIG. 9 shows an end view of the probe of FIG. 8.

DESCRIPTION OF THE PREFERRED EMBODIMENT

Figure 1A:
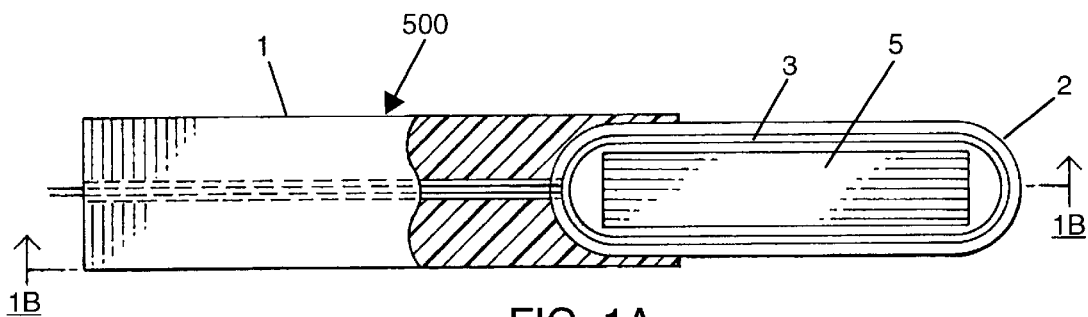
FIG. 1A is a top cross-section along the longitudinal axis of a rectangular probe wherein the coil core is positioned within the metallic specimen support with a fluid tight seal formed by casting.

With regard to receptors sensitive to inductance, it is recognized that inductance L of a coil is the quantity to be measured electrically. This quantity is dependent on the square of the number of turns N and the reluctance of the coil:

$$L = \frac{N2}{RM}$$

The reluctance of a coil surrounded by iron is the length of the wave s of the field lines, divided by the plane A multiplied by the magnetic field constant $\mu o$ X the degree of permeability $\mu r$.

$$RM = \frac{s}{\mu o \, X \, \mu r \, X \, A}$$

The quantity which influences the inductive receptor described herein is the length of the wave s and the degree of permeability $\mu r$.

In a simplified form, an inductive probe to serve as the corrosion measuring probe consists of a coil wrapped on a spool or iron core which is the specimen which changes external measurements by corrosion or erosion.

The magnetic field lines run in three different areas, namely within the iron (sFe, AFe), in the air within the coil (s,A), and finally upon their return in the air exterior to the coil (sa, Aa). The magnetic resistance of the sensor is:

$$RM = \frac{s\text{Fe}}{\mu o \, X \, \mu r + A\text{Fe}} + \frac{s}{\mu o \, X \, A} + \frac{sa}{\mu o \, X \, Aa}$$

The first term on the right side of the equation is very much smaller due to the degree of permeability $\mu r$ of the iron in the denominator having a value of 1.000 to 10.000 and can thus be neglected. Also the third term can be neglected as the section area Aa available for the return wave is much bigger than the plane A inside the coil. In certain cases it is also possible to cover the coil with soft iron, within which the field lines would run practically without resistance. Therefore, only the iron free distance s within the coil is relevant for the reluctance, expressed as:

$$RM = \frac{s}{\mu O^* A}$$

and the inductance of the probe, expressed $$L = \frac{\mu^* A^* N^* N}{s} = \frac{k}{s} \quad \text{with } k = \mu o^* A^* N^* N$$

is lower, the more the iron-core (metallic specimen) inside the coil is diminished by corrosion or erosion. It depends on the iron-free distance s in the denominator, whereby the characteristic record of findings forms a hyperbolic shaped line. Sensitivity $$E = \frac{dL}{ds} = -\frac{\mu o^* A^* N^* N}{s^* s} = -\frac{L}{s}$$

is also reduced with the increase of s. The relative change of the inductivity and relative change of the wave are identical with reversed premises, as the foregoing equation can be restated and expressed:

$$\frac{dL}{L} = -\frac{ds}{s}$$

The theory of the new corrosion measuring method having been explained, the following discussion will serve to differentiate the invention from former technology and to show advantages over the known state of engineering in this field.

The essential advantages of the new technology over the former method, direct resistance measurement on the specimen itself, include the following.

The inductive resistance is extensively indifferent to variations or gradients of temperature. In order to consider the interference factors due to the dependence on temperature of the direct current which are low in comparison to the level of the measuring signal which is delivered by the sensor in this method, the same can be determined easily by using direct current in the coil of the sensor and making appropriate compensation. The sensor being disclosed herein is indifferent to irregular corrosion, for the mass of the metallic specimen can be influenced by magnetic fields, particularly iron, which is disposed so that the coil is under the influence of the magnetic field and the changes of its mass are determined; whereas for E/R measurements, the sectional area of a wire loop can differ greatly dependent on length because of pitting corrosion.

The precision, sensitivity and resolution of the new method for measurement is approximately 1,000 times greater vis-à-vis the changes of direct current resistance used in the E/R measurements method prevalent in the prior art.

In the method of my invention, electrically conductive depositions from the fluid are irrelevant, since there is no contact between the medium and the electric coil. Furthermore, magnetic measurements are taken and not a direct resistance of the specimen itself.

The galvanic isolation of the conducting coil from the fluid medium reduces danger from explosion. Also, the cathodic protection against corrosion is not disrupted by my method. And my method enables optimized measuring results, because influences dependent on design and dimension of the specimen, coil and sensor, and influences due to alternating current as well as those influences inherent in the medium itself can be respected from case to case at a constant measuring range, particularly by choosing the corresponding frequency. This characteristic of my method leads to improved computation of measuring data, for a large part of the measuring range can always be used.

Due to durably constructed probes and their magnetic sensors, a large range of applications in the field of corrosion control and protection against corrosion can be considered.

Furthermore, the following advantages of the new method can be named. The method can also be used for electrolytes which are non-continuing with low ionic content, for the process provides a linear curve for inductance relevant to corrosion. The method enhances opportunity for calibration gauging with weight measurement. All current carrying conducting elements of my device are sealed against contact with the corrosive fluid medium.

If the diminution of the metallic mass by corrosion is exceeded, the energy or power supply for the sensor can be automatically shut down. This represents an additional security particularly in explosive media. Such a shut off or shut down will gives clear indication that the entire probe has to be replaced.

Due to the high flexibility and adaptability of the method, forms and dimensions of specimens now in use as well as wall openings to containers and pipelines can remain in use; and, my method thereby allows adaptive optimization of measuring without requiring any construction changes.

A disadvantage which will be minimized in practice when the method is used inside metallic pipeline and container systems should be mentioned. The new method is sensitive to strong exterior magnetic fields and, therefore, respective shielding may be necessary.

Practical use of the new method and the device will be for fluid media conducting and/or storing/stocking systems, whereas the fluid media can range from highly concentrated electrolytic solutions, acids, bases, complex molecules, organic acids, from saline solutions up to weak electrolytes, such as tap water or other water, organically stressed waters, waters conducting abrasive sands or mud, turbid waters, suspensions and organic and biogen liquids and emulsions, such as petroleum, oils, organic solvents, agricultural liquids, such as milk, stals, washing waters and the like, and finally gas, including hot gases, waste gas, smoke, dust with acid or alkali and/or reductive or oxidative characteristics.

My method is of special interest with regard to components which are exposed to corrosive fluids and those which contain and conduct fluids, such as containers and pipeline walls, fittings, ventilators, valves, etc. These parts are primarily made of metals or alloys of ferromagnetic or materials influenceable by magnetic fields, especially iron based materials and steel products.

As an example for characteristic magnetic dimensions, the density of field lines or susceptibility of the field can be designated; the field size relative to changes of specimen mass by, for example, mounting Hall Effect Devices, chips sensitive to magnetic fields or "squids" into the coil/specimen-system, whereby the field dimension, density and size can be calculated.

It is preferable, particularly with regard to an optimal measuring or corresponding loss of mass of the actual corrosion by the sensor system used and the corrosive medium and the components exposed to it, to expose the coil of the sensor to a preferably sinusoidal alternating current with a frequency in the range of 100 to 300s-1, more preferably from 150 to 250s-1.

In order to determine the loss of mass of a specimen due to corrosive effect of an aggressive medium and to allow exact conclusions on the rate of corrosion, it is advantageous to compensate for external influences, particularly those due to temperature, to sequentially set the coil specimen system of the sensor under direct current to obtain the Ohmic direct current resistance or a similar electric/magnetic measuring figure. And by using the alternating current, it is advantageous to then obtain data for total resistance or a similar electric/magnetic measuring figure; and, by calculating the difference between both resistance values, the inductance of the coil specimen system respective to its changes or a corresponding measuring figure is determined.

When the coil probe device is used under conditions of magnetic saturation, the range of magnetization has no upward limit and high flexibility of measuring is guaranteed.

According to the prevailing flux conditions within the receptacle, container, basin, tank, or pipeline where corrosion is to be controlled, it is advantageous to position the sensor and its specimen parallel with, or normal to, the flow direction of the fluid media.

Another important subject of the invention is a device for the determination of the corrosivity and/or erosivity of fluid media, by the change of mass of metallic material contacted by fluids causing corrosion, particularly moving fluid media. The device is especially based on iron, particularly steel, with at least one sensor, the sensor having at least one specimen which is identical or corresponding in its composition and/or structure to the above-mentioned material, which material is introduced into the fluid medium during a given time span. The device of the invention is supplied with electric current and includes a device for the determination of a change, especially loss, of the electric measuring figure corresponding to the mass of the specimen, especially for the performance of the a.m. procedure.

The invention is characterized by a device having at least one probe having one sensor with at least one specimen, preferably as a core and/or yoke, within the magnetic field, with at least one coil supplied with and conducting alternating current at a predetermined frequency, form and level of amplitude; and, at least one device connected with the coil specimen system of the sensor for the determination of its magnetic size of core, especially its inductance, particularly inductive resistance.

The device of the invention is preferably constructed to allow for an integrated statement about the change of mass due to the corrosion of underground components, for example the moving fluid medium in a pipeline or the like, the device being positioned at right angles to the direction of the fluid flow.

If a measurement should take place on a surface being in the direction of the moving fluid, a probe having a sensor support in the form of a rod with a measuring sensor mounted on the distal end of the rod crosswise to the axis of the probe with a flat round disc formation and arranged windings in the support of the specimen integrated tight to the medium, preferably flat induction coil, is advantageous.

It should be mentioned here that is possible that the described corrosion sensors used in the specimens due to the described flexible design can also be commercial probes and sensors actually in use, that is the s.m E/R sensors, furthermore forms and measurements corresponding to the common "coupon" trial lamellas, i.e., rectangular or round lamellas.

Another advantageous form of construction designed for hydrodynamics is achieved with a cylindrical specimen.

With a specially favorable design of a coil with a core inside of the sensor with a cylindrical specimen, very distinct differences of signal heights, whereby higher precision of the measuring results can be achieved.

If it is possible in any with regard to the condition of temperature and medium also in view of a simpler and thus less costly design, which also guarantees a high flexibility concerning the form, design and dimension of the coil itself and the positioning of the specimen and also for the support of the sensor, the use of medium internal, permeable and thermostable material, for example, based on silicate, especially polymers or synthetic material is advantageous.

The following synthetic materials are for example recommended: polypropylene, acrylic resins, alcrydic resins and especially epoxy resins.

In order to reduce the risk of corrosion and erosion of the support for the specimen, it is advisable that the specimen and probe supports consist of synthetic material with a corrosion and/or erosion inert layer and/or armoring made of hard ceramic material.

Preservation of the tightness of the construction against aggression of the medium and thus the galvanic separation of the coil and the fluid, it is very advantageous, if the coil and/or the specimen is cast in to the mass of the support of the sensor/specimen.

For this reason, it is advantageous to provide a strong adhesion between the surface of the specimen and the windings of the coil to be bedded fluid tight and the fluid polymer, when bedding the coil and/or specimen into the hardening synthetic material and to prevent it from shrinking during the end of polymerization for hardening of the masses.

The a.m. form of construction with a support of the probe in the form of a hollow rod, which facilitates on the one hand the positioning of the specimen in the defined zone of the cross-section of a fluid-conducting element, and on the other hand also facilitates the mounting from outside, is especially advantageous in view of the mechanical preservation and fluid tightness, if the supply and/or control conductors of the sensor and the coil specimen system and its measuring data conductors traverse through the support of the probe, particularly through a hollow of same.

The advantage is especially relevant if the support of the probe contains more than one corrosion measuring probe and therefore a bundle of conductors.

Another relevant advantage is a form of construction allowing a direct exchange of hitherto used and actually used E/R probes or probes allowing the weighing of "coupons" in which the support of the sensor with the sensor is built in into a fitting, especially screw fitting, which is compatible with a standardized commercial and/or existing penetration of the container or pipeline wall and is preferably pressure proof tight and insoluble.

With these reliable and also in highly pressure proof versions of available penetration fittings the mounting of the new magnetic measuring sensors into a fluid is possible without modification of existing facilities becomes easily feasible.

In order to determine the corrosivity and/or corrosion profiles in fluids or fluid streams, another advantageous design for the device of the invention has been developed. The support of sensors holds at least two measuring sensors which are disposed a distance from each other and which sometimes have different features.

A supervision, control and adjustment of the measuring data collecting and processing device adjusting itself, which can also be used for other inductance measurements, but has been especially developed for the present procedure and the new device in relation with the present invention and the probes and sensors used in relation with the same, which is especially suitable due to its simple and robust construction, is characterized by a system to be measured in relation to its inductance, especially of the coil specimen system, respectively of the coil of the sensor, is integrated in a preferably closed tension, respectively current supply, measurement and control circuit, which consists mainly in a microprocessor with a control and measurement data collecting and processing program for the output of direct and alternating current with adjustable frequency, form and level of amplitude, preferably in a digitized form, containing a digital-to-analog converter connected with it by the same supply and control conductors, which at its output, is connected through the supply conductor with a controllable analog switch by means of the microprocessor, preferably via a resistor and buffer amplifier, connected to the magnetically sensing, especially inductive, coil specimen system, especially to the coil of the sensor, so that the coil, preferably voltage dropping, with a measurement amplifier, preferably 1:1, is connected on its side with a—in cases multistage differential amplifier, that the entry of the differential amplifier is further connected over a reference line branched off at the switch, with a sample-and-hold device for storage and output of a reference voltage, which has been provided by the microprocessor, to the differential amplifier and that finally the differential amplifier is connected to the microprocessor on its output, preferably over an analog-to-digital converter and a conductor for measuring data and control.

There is a strong relation between the invented procedure and the components, which are designed for it and described above, and the hitherto used method of direct definition of the change of mass, especially the loss of mass of corrosion specimens in form of lamellas or disks or the like and the revolutionary variation of the invention necessitating no adaption of the measuring stations themselves where the inductance sensor is not placed inside the corrosive medium, but exterior to it, thus replacing a scale, for example in a test laboratory, and can be built into the specimen which up to now had to be weighed, whereas the mass respective to change of the mass is determined by means of an inductance measurement and the new device can advantageously be integrated into the above described supply, control and measurement device and thus replace the above described in-situ probe.

The new device for the determination of the mass respective to mass change, especially "coupons", of specimens exposed to corrosive and/or erosive fluids is characterized by at least one, preferably disposed in a shielded housing and by means of conductors with alternating current supplied to the coil, inside of which a support is mounted for an exactly positioned, reproducible reception of a corroded probe with specimen, especially "coupons" and at least one device connected to the coil for supply of the same with current, particularly alternating current, with programmable frequency, form and range of amplitude and at least one device, which is also connected to the coil specimen system for the determination of at least one of its magnetic core sized, especially of its inductance respective to its inductive resistance.

This helps also to speed up the reliable standardized technique of weighing of the corrosion control.

Referring now to the drawing, FIGS. 1A, 1B, 2A, 2B and 3A, 3B, show respectively the top and side cross-section views of the embodiments of in-situ probes and their sensors according to the invention. Thus, several embodiments of the present invention are shown the Figures. The probes 500, in the order of the foregoing figures are disclosed as rectangular FIGS. 1A, 1B; or round as in FIGS. 2a, 2B; or lamella-like and cylindric, closed on one end, form of the specimen as in FIG. 5. On each distal end of the respective sensor-supports formed as a rod, a cylindrical support for the specimen 5 to be introduced into the fluid medium in the following forms:

rectangular, oval (favorable in the fluid stream), crosswise to the streaming direction;

round, disc-shaped, to be positioned approximately in the streaming direction (parallel the direction) of the medium; and a cylindrical test specimen support 2; whereas the cavity within the support 2 is mounted in a sheathing and the specimen 5 in a fluid tight way, (for example sealed by casting) and inside the specimen support 1, (See FIG. 1), the coil 3, preferably a flat coil 3, carries electric current, preferably alternating (AC) current, by means of a conductor (not shown), which conductors are sealed, the openings for the introduction of the coil of the embodiments shown in FIGS. 1A, 1B and 2A, 2B are sealed with the sealing element 4.

Figure 3A:
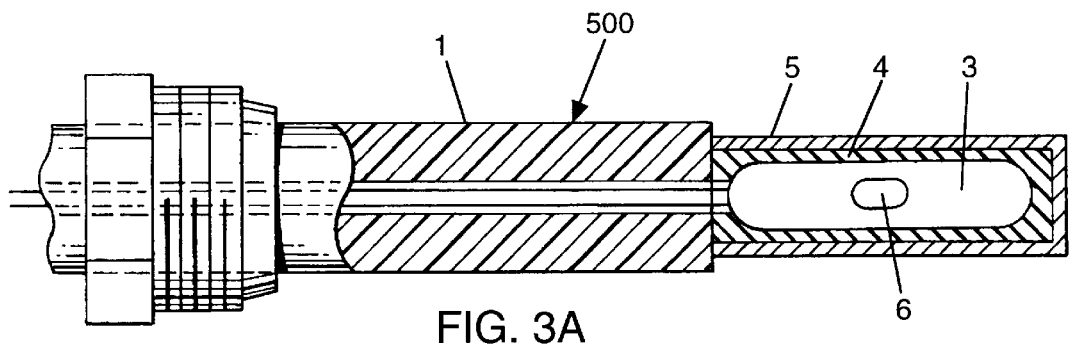
FIG. 3A is a top cross section along the longitudinal axis of a probe compatible with a screw fitting for a standard wall penetration system, wherein the coil core is centrally within the cylindric metal specimen.
Figure 3B:
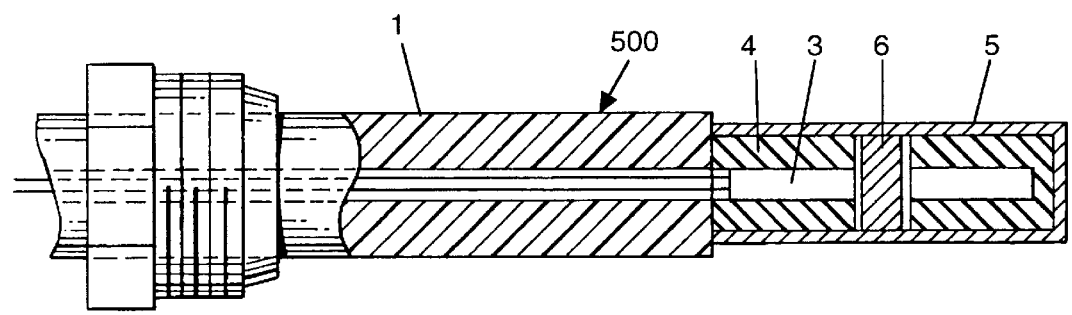
FIG. 3B is a side cross-section of the probe of FIG. 3A.

FIGS. 3A, 3B show how probe 500 may be formed and adapted to be fixed into a compatible screw fitting for a standard wall penetration system. In addition, probe 500 in FIGS. 3A, 3B shows a central coil core, which is tightly connected to the inside of the cylindric specimen 5, thereby essentially forming a core yoke system.

Figure 4:
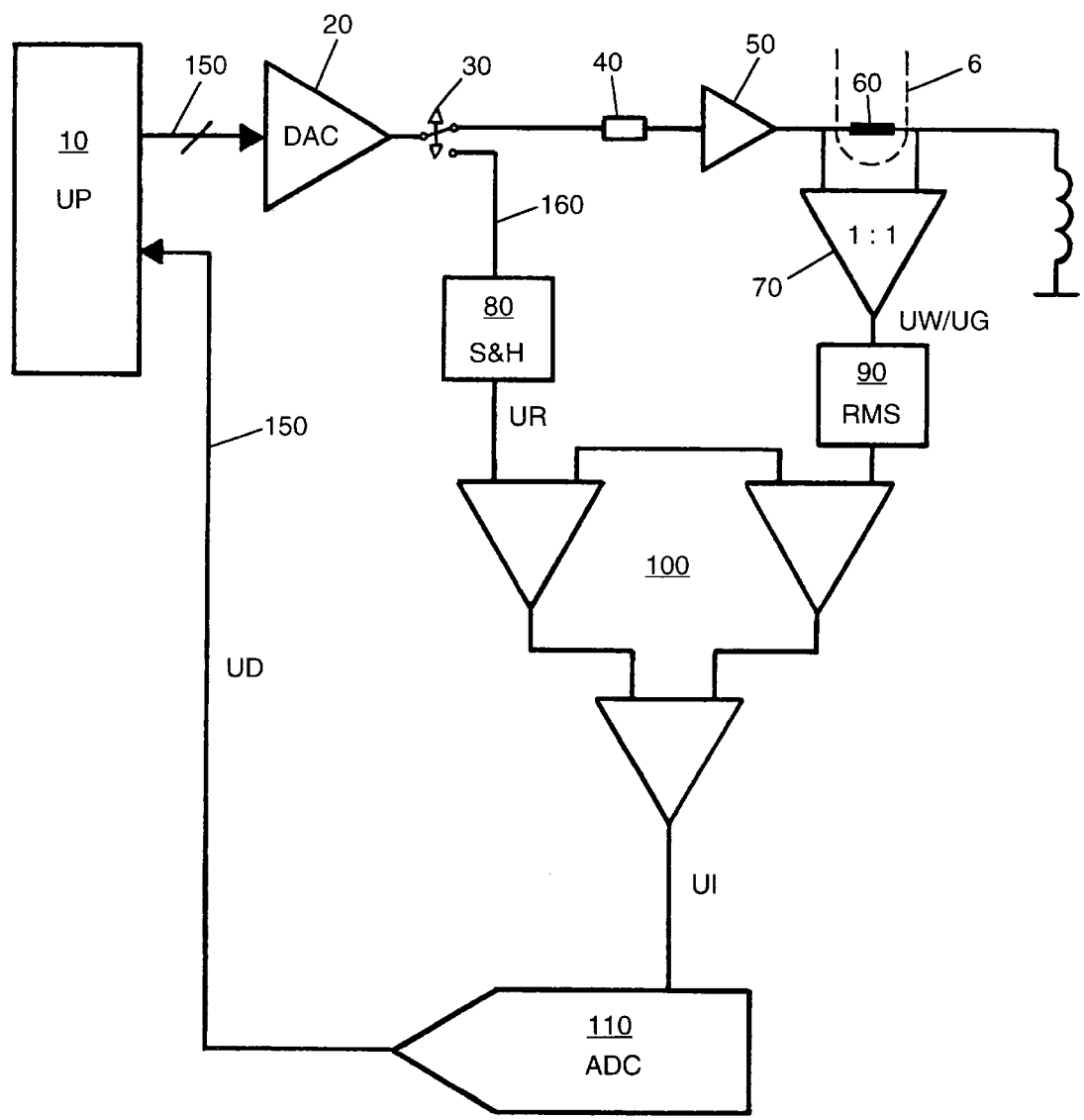
FIG. 4 is a schematic diagram of the new corrosion control device of the invention, wherein a multifunctional microprocessor supplies a digital analog converter whereby the frequency, form and range of amplitude and alternating current are adjusted for measurement and configuration of the measuring instruments; the analogized data transported by a switch to a resistor and an amplifying buffer into a coil of the coil metal specimen system of the magnetic sensor contacting the corrosive fluid whereby the specimen sustains loss of mass.

FIG. 4 is a schematic diagram of the device according to the invention with dispositions for supply, control and measurements. FIG. 4 indicates the preferred embodiment for the new corrosion control device, wherein a multifunctional microprocessor 10 supplies a digital-analog converter 20 over conductor 150 and, preferably, adjusted for the measurement and configuration of measuring instruments, the frequency, form and range of amplitude and alternating current, which is then analogized and, by means of switch 30, is transported over conductor 160 to a resistor 40 and a buffer amplifier 50 into coil 60 of the previously described coil specimen system of the magnetic sensor 6, shown here in a dashed line, which is in contact with the corrosive fluid and suffers the loss of mass.

From coil 60 the voltage UW, corresponding to the total resistance, that is, the sum of the inductive and Ohmic resistance, is taped over two conductors which are not described herein and lead to the 1:1 amplifier 70.

For obtaining a second reference value comparable to the alternating current, the microprocessor 10 supplies direct current from coil 60 of predefined resistance and not a direct current UG corresponding only to the pure Ohmic direct current resistance of the sensor system is supplied to the 1:1 amplifier 70, from where both values of the voltage drop UW, UG, which result of the introduction of alternating and direct current, reach the differential amplifier 100, where the finding of the difference between the two values is made and the voltage UI corresponding to the inductance of coil 60 is calculated.

This inductance current UI is compared in the differential amplifier 100 to a reference voltage UR, which is conducted to the same, and also controlled by microprocessor 10, by conductor 150, DAC converter 20, alternating switched by switch 30 and reference conductor 160 with sample and hold storage device 80 and if different values appear between reference voltage UR and temperature compensated reactive voltage UI, this difference signal UD is transmitted to microprocessor 10 which does the measurement itself, via the ADC analog digital converter 110 with 20,000 steps and conductor 150. The microprocessor 10 carries out the adaption of the reference voltage according to the difference of the signal UD as long as the difference of the signal UD with which it has been supplied, equals zero.

If there is a loss of mass of a specimen of probe 6, this changes its inductance, and also the taped UW, the resulting voltage UI and an adjustment of the signal by the microprocessor for the reference current UR has to take place due to the difference signal, UD, coming through via the feedback control conductor 150.

The number of adjustments steps per unit time respective to the change of the reference current UR is a measure of the change of mass, caused by the corrosion of the specimen, which can then be easily determined. Consequently a device is provided having a closed control loop, being universally applicable.

Figure 5:
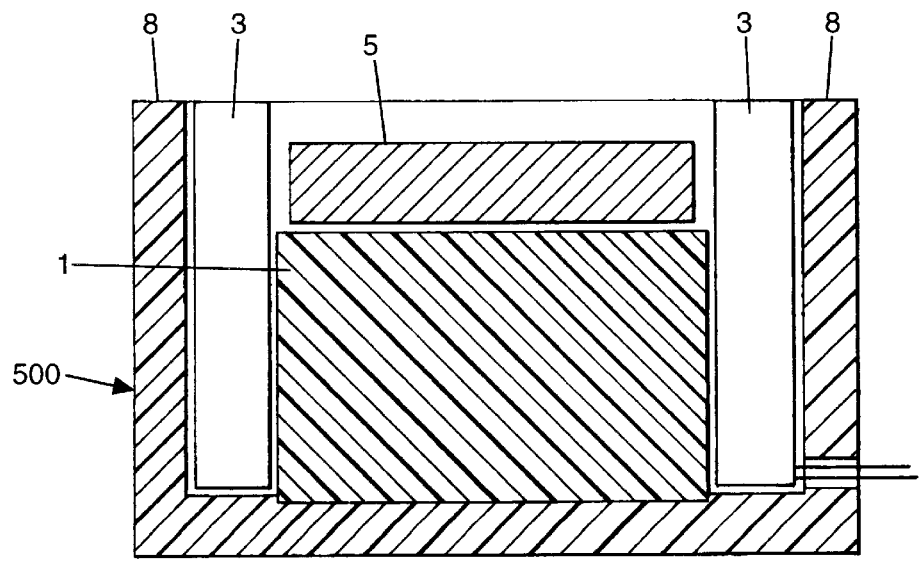
FIG. 5 is a side cross-section of a specialized embodiment of the invention suitable to measure the loss of mass of the specimen, known as "coupon", that metallic specimen positioned transversely within the charged coil, but although differently dimensioned and configured, is operative identically as the inductance probes shown in FIGS. 1–3 above.

The device shown in FIG. 5 is a special variant of the invention and is suitable for the determination of the loss of mass of a specimen 5, also called "coupon" 5, which has been taken out of a corroding system where it has been exposed itself or a time span to the medium and represents a probe 500 outside of the corrosive medium. Its sensor 100 is, even if differently dimensioned and configured, completely identical to the inductance probes heretofore described.

In a shielding housing 6 is a coil 3, which is supplied with alternating current through a conductor (not shown), on the inner side of which housing a highly reproducible coupon 5 is mounted inside of coil 3, whereby coupon 5 represents here a "coil core" which is heavily altering the coil inductance 3 by its change of mass due to corrosion. Suitably this dry sensor 500 is integrated into a device in accordance with FIG. 4.

Figure 1B:
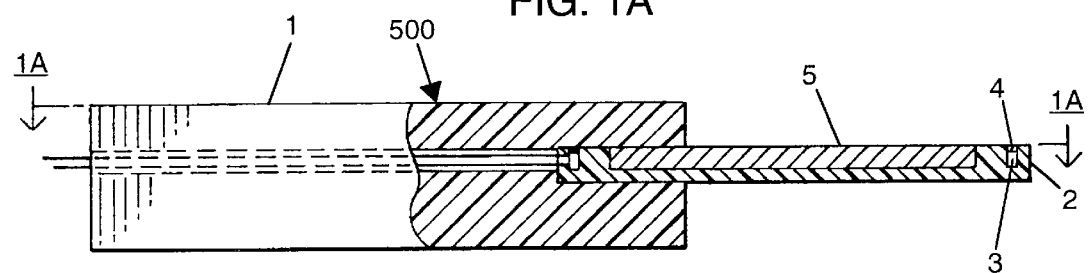
FIG. 1B is a side cross-section along the longitudinal axis of the probe shown in FIG. 1A.

This probe 500 for the embodiment of FIG. 1A and FIG. 1B is comprised of an insulated hollow handle 1, which has a cavity as shown running through the length of its central portion. This longitudinal cavity serves as a conduit through which coil leads (not shown) are run. The flat rectangular sacrificial element 5 (also referred to as the specimen) is centered within the ovately wound coil 3. The coil and sacrificial element are encapsulated ovately with an Epoxy or silicone encapsulant 2 and the coil 3 is also protected by non-corrosive seal 4. In this embodiment, the surface of sacrificial anode is fully exposed to the environment whose corrosivity it is adapted to measure. In typical use, when immersed in a fluid medium, if the flow stream is directed toward or orthogonal to the surface of the sacrificial anode, it is positioned for the best measurement of erosion. If the flow stream is tangential to anode surface, it is in position for the best measurement of corrosivity.

Figure 2A:
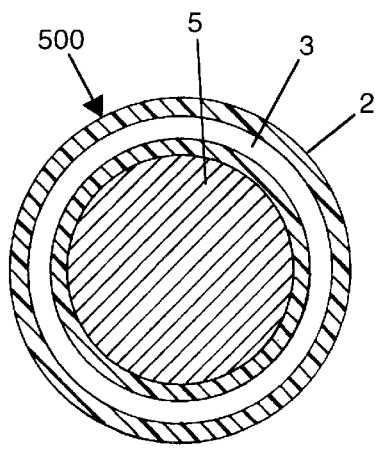
FIG. 2A is a top elevation of a round or disc-shaped probe to be positioned parallel with the direction of a moving fluid.
Figure 2B:
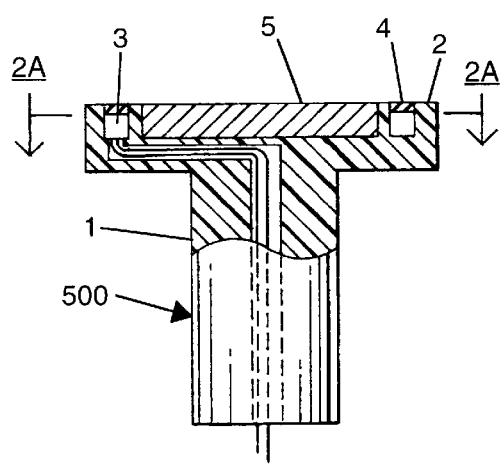
FIG. 2B is a side cross-section view of the round or disc-shaped embodiment for the probe of FIG. 2A.

The Probe 500 shown in FIG. 2A and FIG. 2B are the top and side cross-section views of an alternative embodiment for the present invention. Depicted is a circular disk shaped (lamellar) sacrificial specimen 5, which is centered within the circularly wound coil 3. In this embodiment, the coil is recessed within the encapsulant 2 and subsequently protected from the fluid medium by the insulated layer of seal 4. The entire assembly is attached to the hollow handle 1. The sacrificial element again has one side exposed to the fluid medium. The use of this embodiment is the same as was discussed for the embodiment shown in FIG. 1A and FIG 1B in the preceding paragraph.

FIG. 3A and FIG. 3B are still another embodiment for this invention; FIG. 3A is the top cross-section along the longitudinal axis and FIG. 3B is the side cross-section of the same. In this embodiment it is designed to be compatible with a screw fitting for a standard used system. Again, the coil 3 is a flatly wound rectangular shaped coil (racetrack shaped). Centrally mounted within is a metallic core 5 to transport the lines of flux to the outer cylindrical shell 5, which in this embodiment is the sacrificial anode or specimen. An encapsulant 4, such as a potting compound is used to protect the coil from being corroded by the fluid medium.

FIG. 5 is a side cross-section along the longitudinal axis of a specialized embodiment that uses the principles of the present invention. The coil assembly is essentially shielded by the enclosure 6. Within this enclosure is the coil 3, the insulated specimen support 1, and the specimen 5. The loss of mass is determined in the same manner as discussed below.

Regarding the process of corrosion, corrosion is the action, process or effect of corroding. Typically, it is a gradual loss of metal or alteration by a chemical or electrochemical process, being essentially an oxidizing process, as in the atmospheric rusting of iron.

Erosion is produced commonly referred to as the gradual progressive loss or surface destruction of a hard substance through abrasive action. Chemically, erosion occurs through the abrasive action of a moving fluid or gas, and is accelerated by particles that are held in suspension.

There are many geometrical configurations that can be used in the principles discussed and for the four examples that are shown. Basically, the coil induces a sinusoidal voltage into the metallic core. Specifically, in FIGS. 1, 2 and 5, these induced sinusoidal voltages cause a circulating current to flow circularly within the sacrificial anode. The path and current density within this core are functional with the applied frequency. For example, the higher the frequency, the closer to the surface of the circular path is taken by these circulating currents. Conversely, the lower the frequency of excitation, the greater is the depth of the circulating currents. These circulating currents are more commonly referred to Eddy currents.

These circulating currents in turn give rise to counter emfs that oppose the initial direction, thereby yielding a resultant change in inductance, which provides an extremely sensitive measurement of corrosion or erosion caused by the reduction or loss of metal within the specimen or sacrificial anode.

Specifically, the loss of mass is easily determined by the change of inductance as detected by the coil. This loss of mass is a direct measure of the corrosion or erosion that had taken place. For example, when the system is first placed in operation, an initial measurement of the inductance is made. After several hours of operation, another reading of the inductance is made. Perhaps the measurements need only be taken after several days or even months, depending upon the corrosivity of the fluid medium. These changes of inductance are then a direct measure of the loss of metal within the metallic specimen which is inversely proportional to the rate of change of corrosivity and/or erosivity.

With reference to the embodiment shown in FIG. 3, the coil is surrounded by a cylindrically shaped canister that acts as the sacrificial anode. Even though this embodiment is slightly less sensitive, the coil assembly is metallically shielded which protects the sensor from extraneously induced objectionable interferences.

In all cases, the coil structure must be encapsulated to protect it from the corrosive environment. Should the coil become corroded, the subsequent measurements would be in error, as well as to cause damage to the coil itself.

Restating again the measure of corrosion is best determined by placing the probe in the fluid stream so that the flow is tangential to the surface or the sacrificial anode. It is also true that best measure of erosion can be obtained when the fluid flow is directed towards or orthogonal to the surface of the sacrificial anode. However the probe embodiment of FIG. 3 is best suited in applications where there may be corrosive and erosive chemical actions present.

Two principal measurements are made to determine the corrosivity and/or erosivity. They are: (1) the DC ohmic resistance, R, of the coil and (2) the impedance, Z, of the coil.

In the measurement of the DC resistance of the coil, a steady state direct current voltage is applied as the excitation to the probe coil. The current that flows through the coil is sensed by the voltage drop across the current sensing resistor. It then follows that:

$$R_{dc} = \frac{E_{dc}}{I_{dc}}$$

To determine the impedance Z of the coil, a steady state sinusoidal voltage, of frequency f is then applied as the excitation to the probe coil. Therefore:

$$Z = \frac{V_{ac}}{I_{ac}}$$

and $$Z = SQRT(R^{}2 + (xL^{}2))$$

Because the changes of inductance, L are a direct measure of the loss of metal within the metallic specimen, it then follows:

$$X1 = SQRT(Z^{}2 - R^{}2)$$

$$L = \frac{X1}{2*Pi*f}$$

which is inversely proportional to the rate of change of corrosivity and/or erosivity.

The present invention further discloses an improved corrosion measurement system for determining the rate of corrosion of a fluid medium. The system is comprised of a highly sensitive excitation and amplification electronic circuitry for registering and displaying the stable and accurate measurement results.

The unique unitized measurement probes are temperature stabilized using thermally inertially balanced metallic probes; the first reference element being coated with an impermeable insulating coating, the second, the corroding element, being fully exposed to the corrosive fluid.

Figure 6:
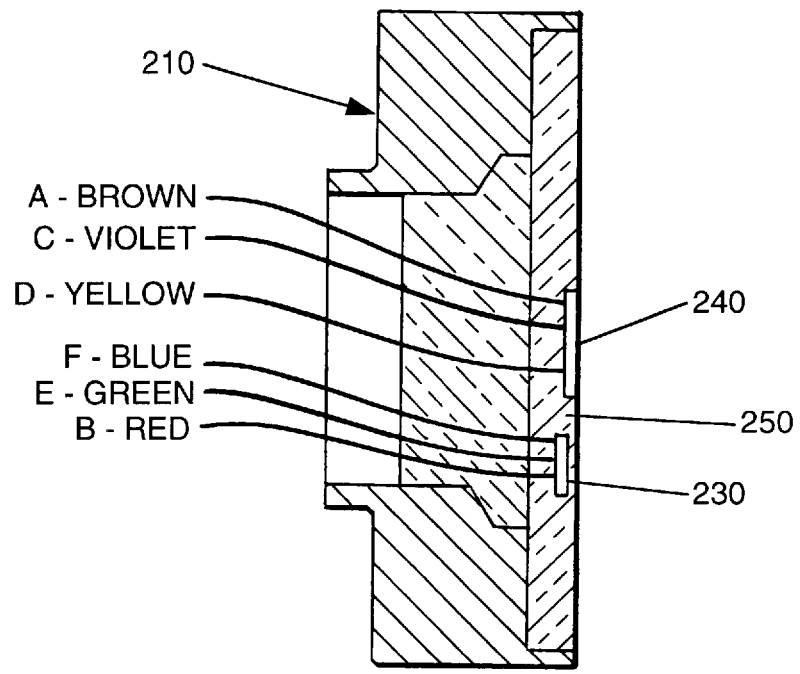
FIG. 6 depicts a side elevation of the unitized measurement probe of the preferred embodiment. This probe is a total immersion probe.
Figure 7:
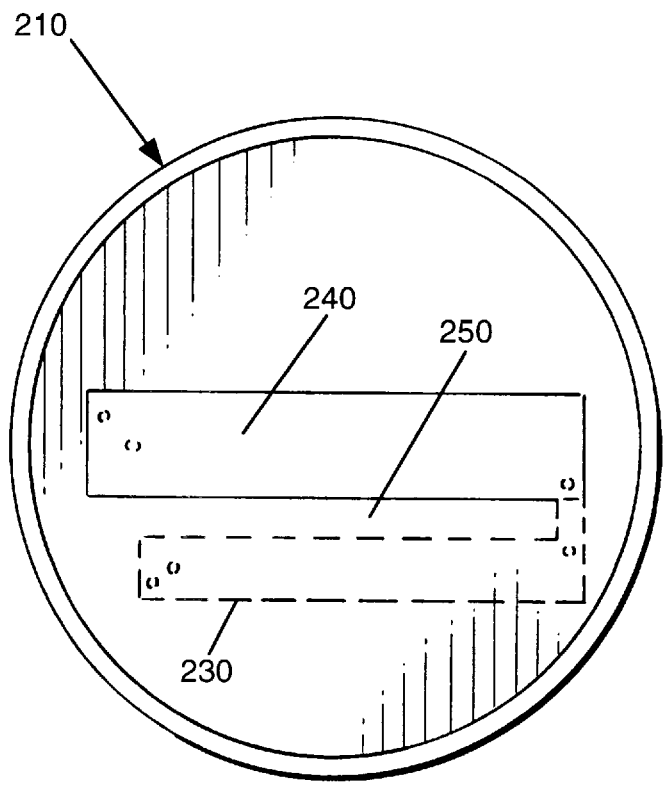
FIG. 7 shows an end view of the probe of FIG. 6.

As shown in FIGS. 6 and 7, the preferred embodiment of the present invention is comprised of a total immersion probe 210 consisting of a reference element 230 and the corroding element 240. A conformal protective coating 250, that protects the reference electrode from the corrosive activity of the fluid medium, completely covers the entire exposed surfaces of the reference electrode 230.

When the probe is immersed in the corrosive fluid, there is a loss of metal in the corroding element. This loss of metal manifests itself as an increase in the resistivity of this electrode. This increase is then registered by the highly sensitive electronic measurement circuits to ultimately display the results on the liquid crystal display.

Shown in FIGS. 8 and 9 is the detailed assembly of an alternate embodiment of a partial immersion probe 220, where only the probe end comes in contact with the corrosive fluid medium. The probe body is shaped cylindrically as illustrated in FIG. 9, where only the probe tip are immersed into the corrosive fluid medium.

Figure 10:
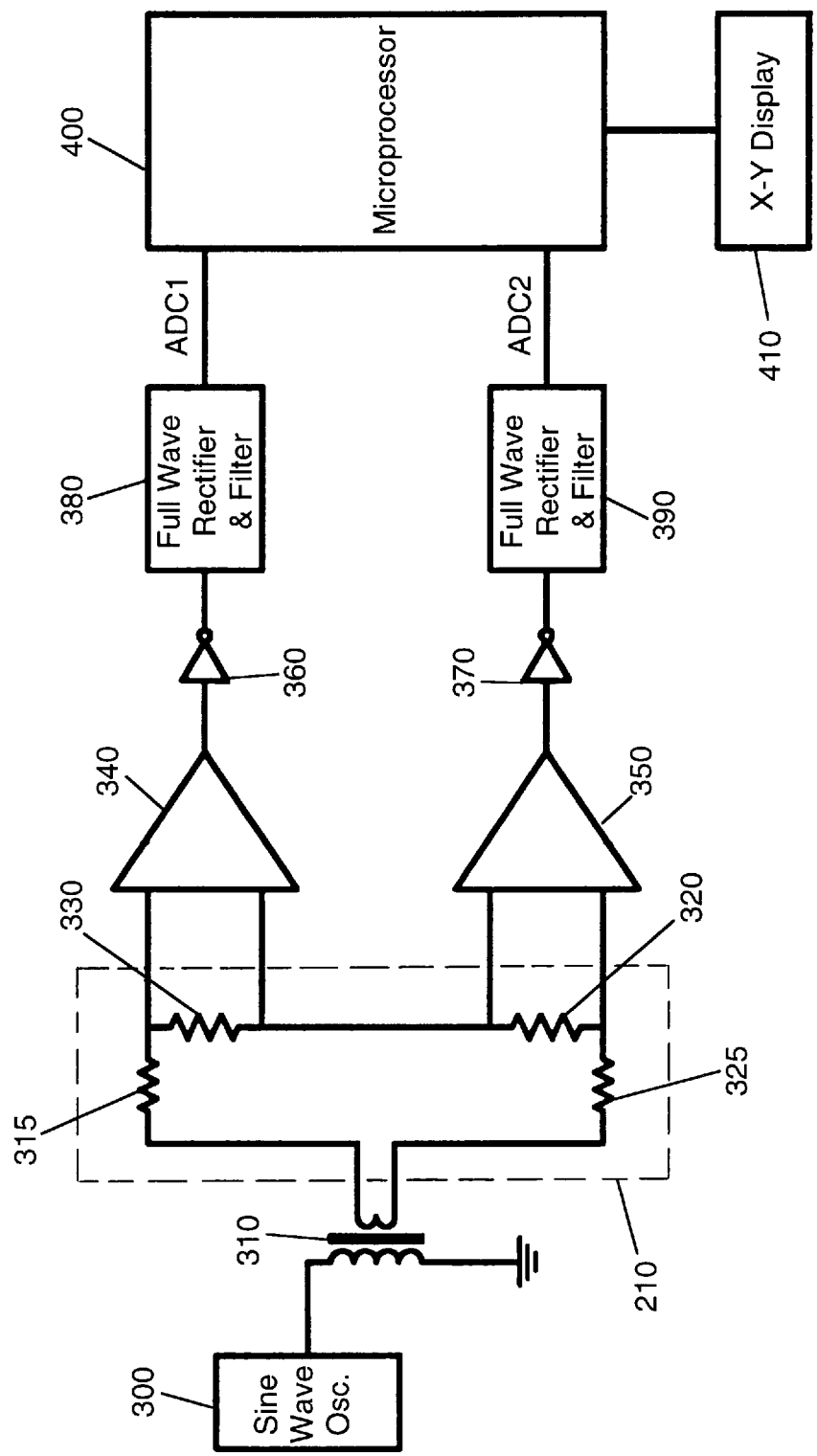
FIG. 10 is a block diagram of the electronic circuitry of the improved corrosion measurement system.

Turning now to FIG. 10, depicted is schematic block diagram of the electronic measuring circuits for the corrosion measurement system. A Wien bridge oscillator 300, preferably oscillating at a frequency ranging from 700 to 900 Hertz, provides the excitation voltage for the measuring circuits. Oscillator 300 generates a low distortion sinusoidal waveform to drive the primary winding of coupling transformer 310. The output voltage provided by the oscillator is nominally 2.83 volts RMS.

The primary of the transformer 310 is rated at 50 milliamperes. The transformer as used is a step down transformer with a turns ratio nominally of 463 to 1. The DC resistance of the secondary winding is nominally 30 milliohms. The output of the secondary connects to the unitized probe at wiring points A and B respectively. Points A and B connect to the serially connected resistors 315 and 325, respectively. Also, in series with resistors 315 and 325 are the reference element 230 and the corroding element 240.

It is ideally suited to have the serially connected elements have the same current flowing through them. Any variations in the current flowing through them, because of amplitude fluctuations in the power supply or in the oscillator will be nullified when the subsequent ratiometric measurement that follows is made. Also, because both elements are within the same unitized probe, are made of the same metals and have the same mass, the thermal inertia of these masses is compensating, where the thermal drift due to the changes of resistance of the reference and corroding electrodes, is also compensating and the thermal drift readings, are nullified in the same manner.

The reference channel differential amplifier 340 amplifies the voltage drop across the reference resistance 330 and the corroding channel differential amplifier 350 amplifies the voltage drop across the corroding element resistance 320. Cascaded from the output of each differential amplifier are buffer amplifiers 360 and 370. Separate Full-Wave Rectifiers-and-Filters 380 and 390 follow at the outputs of buffer amplifiers 360 and 370. The outputs of each Full-Wave Rectifiers-and-Filters 380 and 390 connect to the Analog-to-Digital Converter inputs, ADC1 and ADC2, of microprocessor 400.

Compensation for variations in temperature of the measuring circuitry is accomplished by switching from the reference channel to the corroding channel before each measurement is made. The initial offset that was measured is subsequently subtracted from each of the corroding measurements taken for the removal of the temperature differential. Display 410 shows a graphic, real time presentation of the results obtained from the measurement, as shown in FIG. 11.

Figure 11:
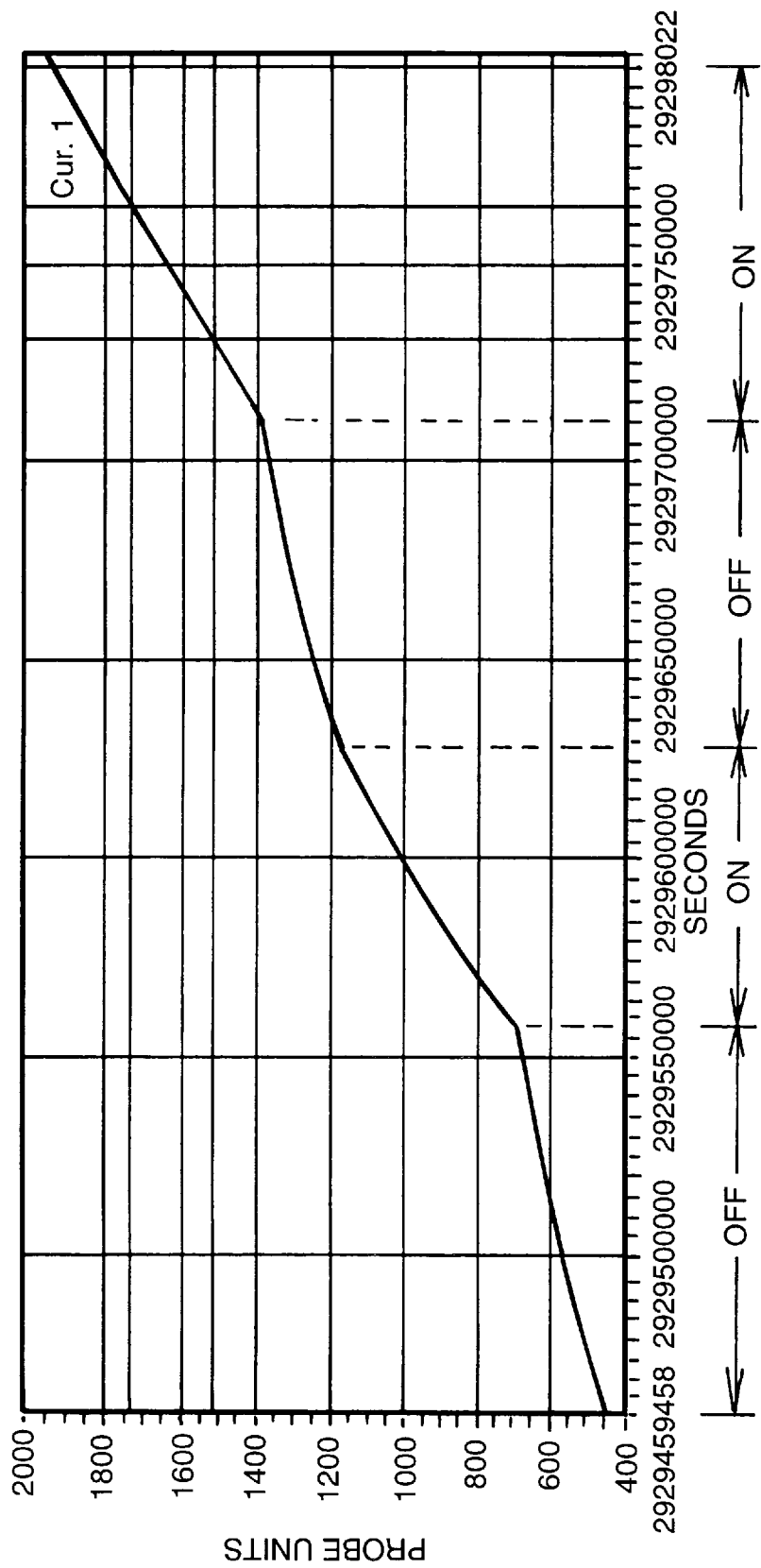
FIG. 11 is a performance graph detailing the improved sensitivity of measurement.

FIG. 11 is a graph that best illustrates the performance of the system. The abscissa is in units of seconds and the ordinate, in probe units.

Shown is the results of a particular test that bests illustrates the improved sensitivity of the corrosion measurement. The graph shows four slopes. The slope shows the corrosion rate in mils per year, equating 0.001"/year thinning of the metal sensor element. The first slope is for a nonaerated condition, whereas the second slope results when the corrosive solution is aerated. The third slope is nonaerated and the fourth and final slope, aerated.

An air bubbler is placed in the corrosive fluid and is turned off and then on, in repeated cycles to demonstrate the quality of measurement. With the air bubbler off, the corrosion rate is 2.9 and with the air bubbler on the rate of corrosion increases to 6.7, with a corresponding metal loss of 0.004277. Two complete cycles on-off cycles are shown. The slopes of each on-off period indicate the improved repeatability of measurement. Being a test that is performed in real-time, the sensitivity and repeatability of measurement are clearly shown in the accompanying graphical results in FIG. 11.

Figure 12:
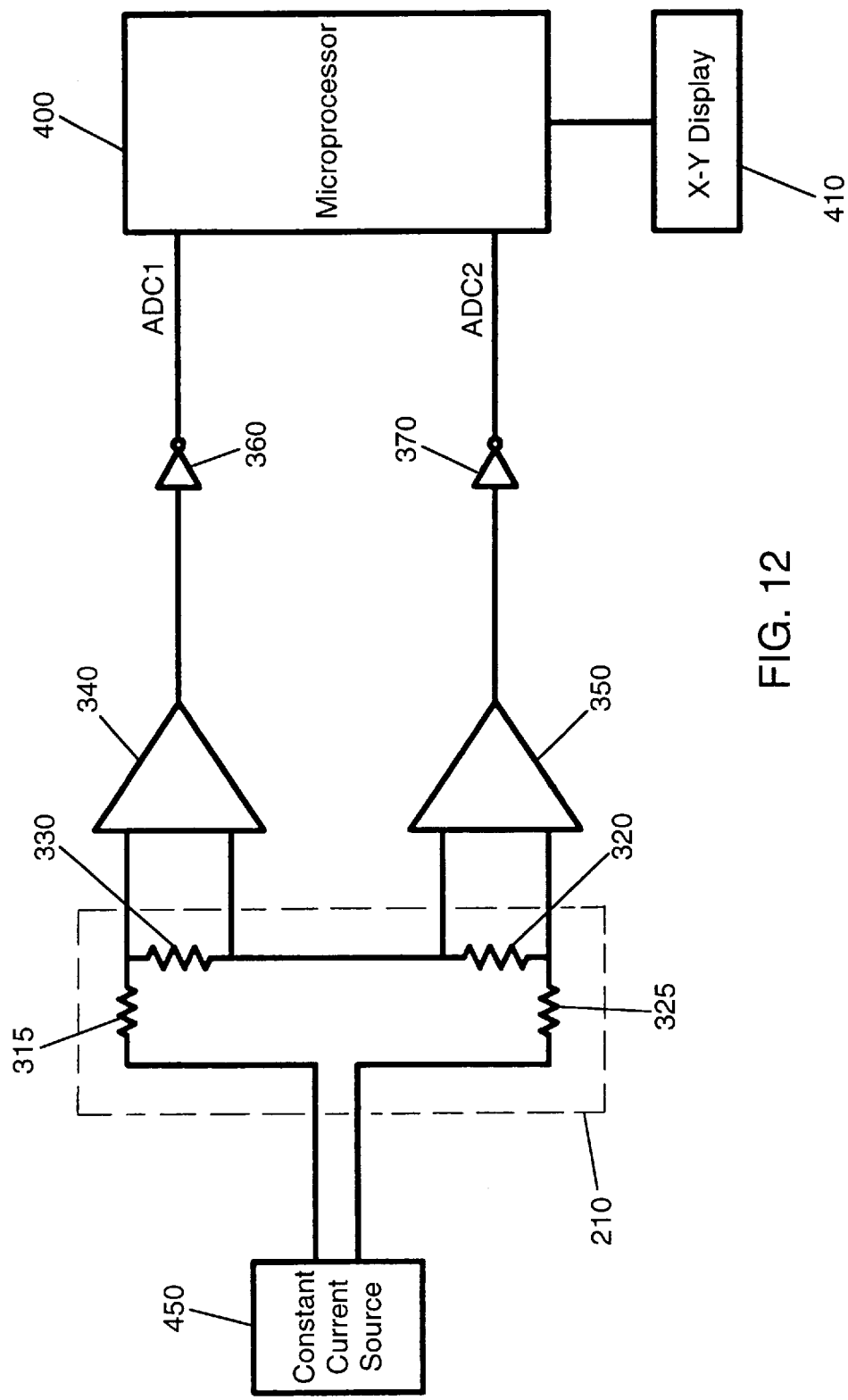
FIG. 12 is a block diagram of an alternate embodiment of the electronic circuitry of the improved corrosion measurement system.

In an alternate embodiment as shown in FIG. 12, the electronic measurement circuit uses a zero frequency constant current DC source 400. This DC current is preferably between 1 and 5 amperes to provide the source excitation to the unitized probe 210. As is shown in the preferred embodiment, the reference channel differential amplifier 340 amplifies the voltage drop across the reference resistance 330 and the corroding channel differential amplifier 350 amplifies the voltage drop across the corroding element resistance 320. Cascaded from the output of each differential amplifier are buffer amplifiers 360 and 370. The outputs of each buffer amplifier 360 and 370 connect to the Analog-to-Digital Converter inputs, ADC1 and ADC2, of microprocessor 400. The results of the measurement are presented graphically on display 410.

While specific embodiments of the present invention have been shown and described in detail to illustrate the principles of the invention, it should be understood the that other modifications or embellishments can be made without departing from the true spirit of the invention. What is desired to be protected by Letters Patent is set forth in the appended claims.

What is claimed is:

1. A corrosion measurement system for use in a particular corrosive medium to obtain measurements for determining a rate of corrosivity of the medium, comprising:

a probe having a reference element and a corroding element, each element having identical physical properties, the probe adapted for contacting the corrosive medium, the reference element having a conformal coating that protects the reference element from exposure to corrosivity of the medium, and the corroding element fully exposed for corrosion by the medium;

a measuring circuitry with a power source associated with the elements of the probe for measuring a rate of corrosivity; and, means for instantaneously displaying the rate of corrosivity of the medium, said means in communication with the probe.

2. A corrosion measurement system as described in claim 1, the measuring circuitry power source further comprising an oscillator communicating with the probe for providing an excitation voltage that essentially generates a low distortion sinusoidal waveform through the probe to the measuring circuitry.

3. A corrosion measurement system according to claim 2, wherein the oscillator comprises a Wein bridge oscillator that oscillates within a frequency range from 700 to 900 Hertz.

4. A corrosion measurement system according to claim 3, the measuring circuitry further comprising a step down transformer with a primary winding and a secondary winding, the primary winding driven by the low distortion sinusoidal waveform from the oscillator.

5. A corrosion measurement system according to claim 4, the reference element further comprising a serial resistor and the corroding element further comprising a serial resistor and the secondary winding communicating with the reference element through its serial resistor and with the corroding element through its serial resistor.

6. A corrosion measurement system according to claim 5, the reference element having a reference resistance and the corroding element having a corroding element resistance, the reference element and its associated measuring circuitry comprising a reference channel, and the corroding element and its associated measuring circuitry comprising a corroding channel, each channel having a differential amplifier that amplifies a voltage drop across its respective element resistance, succeeded by a buffer amplifier and full-wave rectifiers and filters connected to a microprocessor having an analog-to-digital converter input respective to each of the channels, whereby changes of resistance of the reference and corroding elements are measured by the microprocessor.

7. A corrosion measurement system as described in claim 6, further comprising a means for compensation for variations in temperature of the measuring circuitry associated with the reference channel and with the corroding channel.

8. A corrosion measurement system as described in claim 7, wherein the means for displaying comprises a display unit associated with the microprocessor for real time read out of the rate of corrosivity of the medium.

9. A probe for use in a corrosion measurement system operative on a particular corrosive medium to obtain measurements for determining a rate of corrosivity of the medium, the probe comprising:
   a probe body with a distal end, a reference element and a corroding element, each element having a terminal end;
   a probe circuitry with a power source to register a resistivity of the reference element and resistivity changes of the corroding element; and,
   measuring circuitry associated with the probe elements of the probe body for measuring the rate of corrosivity; and,
   a means for compensating for thermal and current variations for precision in measuring the rate of corrosivity.

10. A probe according to claim 9 above, wherein the reference element and the corroding element are each constructed of a metallic material that is the same for each element.

11. A probe according to claim 10, wherein the reference element and the corroding element each have a mass which is the same for each element to thermally compensate measurements for determining a rate of corrosivity.

12. A probe according to claim 10, wherein the reference element and the corroding element each have a physical geometry that is the same for each element.

13. A probe according to claim 12, the reference element further comprising an outer surface having a coating of a material that is impermeable to the corrosive medium for protecting the reference element from the corrosive medium.

14. A probe according to claim 9 above, the measuring circuitry further comprising a reference channel connected to the reference element through a series resistor and a corroding channel connected to the corroding element through a series resistor, each channel further having a reference resistance, followed by a differential amplifier, a buffer amplifier, and a full-wave rectifier-and-filter, that communicate with an ADC converter for each channel for input to a microprocessor, to determine an initial offset prior to each corrosivity measurement.

15. A probe according to claim 14, the means for compensating comprising each element having essentially identical physical properties, including shape, mass and material composition, to achieve a thermal inertia for reducing thermal gradients; and, a measured corrosivity reduced by the initial offset to further eliminate temperature and current variations.

16. A probe for use in a corrosion measurement system operative on a particular corrosive medium to obtain measurements for determining a rate of corrosivity of the medium, the probe comprising:
   a probe body with a distal end, a reference element and a corroding element, each element constructed of the same metallic material, having an identical mass and shape, and each having a terminal end; the reference element further comprising an outer surface having a coating of a material that is impermeable to the corrosive medium for protecting the reference element from the corrosive medium;
   a probe circuitry with a power source to measure a resistivity of the reference element and resistivity changes of the corroding element; and,
   measuring circuitry associated with the probe elements of the probe bodyfor measuring a rate of corrosivity measurement results.

17. A probe according to claim 16, wherein the coating material of the reference element is characterized by a high degree of thermal conductivity.

18. A corrosion measurement system according to claim 17, wherein the coating material of the reference element is characterized by a high degree of electrical insulation.

19. A corrosion measurement system according to claim 18, wherein the terminal end of each of the elements is flush with the probe body distal end, whereby the probe is adapted for total immersion in a corrosive medium.

20. A corrosion measurement system according to claim 18, wherein the terminal end of each of the elements projects outward from the probe body, whereby the probe is adapted for measurement of a rate of corrosivity of a medium by immersing the elements only in a corrosive medium.

21. A corrosion measurement system as described in claim 20, wherein the reference element and the corroding element are thermally insulated from the probe body.

22. A corrosion measurement system for use with a particular corrosive medium to obtain measurements for a rate of corrosivity of the medium, comprising:
   a probe having a covered reference element and an exposed corroding element;
   a measuring circuitry associated with the elements of the probe for measuring rate of corrosivity, the circuitry having a zero frequency constant current DC source from one to five amperes; and,
   means for displaying the rate of corrosivity of the medium in communication with the probe.

23. A system to determine the corrosivity of a fluid medium by the changes in a corroding mass of a metallic material respective to a reference mass, while both masses are in contact with the fluid medium, the system comprising:

a probe having a reference element and a corroding element, each element comprising the same material and having the same shape and mass, contacting the fluid medium;

means for protecting the reference element from corrosion by the fluid medium surrounding the reference element;

means for supplying the system with an electrical current, for providing an essentially constant reference resistance and a fluctuating corrosion resistance that increases as the mass of the corroding element is diminished by corrosivity;

means for ratiometric measurements of the reference and corrosion resistances associated with the probe, that essentially eliminates influences external to the system;

means for real-time determination of the rate of corrosivity of the fluid medium by measuring and comparing resistance changes of the elements, that are primarily caused by loss of mass of the corroding element; and, means for displaying the rate of corrosivity of the medium in communication with the probe.

24. A corrosion measurement system for use in a particular corrosive medium to obtain measurements for determining a rate of corrosivity of the medium, comprising:

a probe having a reference element and a corroding element, each element having identical physical properties and each element adapted for contacting the corrosive medium;

a measuring circuitry with a power source associated with the elements of the probe for measuring a rate of corrosivity; the measuring circuitry power source further comprising a Wein bridge oscillator that oscillates within a frequency range from 700 to 900 Hertz, the oscillator communicating with the probe for providing an excitation voltage that essentially generates a low distortion sinusoidal waveform through the probe to the measuring circuitry, and a step down transformer with a primary winding and a secondary winding, the primary winding driven by the low distortion sinusoidal waveform from the oscillator.

means for displaying the rate of corrosivity of the medium in communication with the probe.

25. A corrosion measurement system according to claim 24, the reference element further comprising a serial resistor and the corroding element further comprising a serial resistor and the secondary winding communicating with the reference element through its serial resistor and with the corroding element through its serial resistor.

26. A corrosion measurement system according to claim 25, the reference element having a reference resistance and the corroding element having a corroding element resistance, the reference element and its associated measuring circuitry comprising a reference channel, and the corroding element and its associated measuring circuitry comprising a corroding channel, each channel having a differential amplifier that amplifies a voltage drop across its respective element resistance, succeeded by a buffer amplifier and full-wave rectifiers and filters connected to a microprocessor having an analog-to-digital converter input respective to each of the channels, whereby changes of resistance of the reference and corroding elements are measured by the microprocessor.

27. A corrosion measurement system as described in claim 26, further comprising a means for compensation for variations in temperature of the measuring circuitry associated with the reference channel and with the corroding channel.

28. A corrosion measurement system as described in claim 27, wherein the means for displaying comprises a display unit associated with the microprocessor for real time read out of the rate of corrosivity of the medium.

* * * * *